United States Patent
Kapadia et al.

(10) Patent No.: US 7,611,534 B2
(45) Date of Patent: Nov. 3, 2009

(54) PERCUTANEOUS ATRIOVENTRICULAR VALVE AND METHOD OF USE

(75) Inventors: Samir Kapadia, Orange, OH (US); Jay Yadav, Hunting Valley, OH (US); E. Murat Tuzcu, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 131 days.

(21) Appl. No.: 11/509,469

(22) Filed: Aug. 24, 2006

(65) Prior Publication Data
US 2007/0156233 A1 Jul. 5, 2007

Related U.S. Application Data

(60) Provisional application No. 60/711,233, filed on Aug. 25, 2005.

(51) Int. Cl.
*A61F 2/24* (2006.01)
(52) U.S. Cl. .............. 623/2.17; 623/2.14; 623/1.26
(58) Field of Classification Search ............ 623/2.1, 623/2.14, 2.34, 2.11, 2.18, 1.24, 1.26, 1.35, 623/2.12–2.19, 2.36–2.38; 600/37; 606/151
See application file for complete search history.

(56) References Cited

U.S. PATENT DOCUMENTS

| | | | | |
|---|---|---|---|---|
| 5,728,152 A * | 3/1998 | Mirsch et al. ............... 623/2.1 |
| 5,902,317 A * | 5/1999 | Kleshinski et al. ......... 623/1.18 |
| 6,409,750 B1 * | 6/2002 | Hyodoh et al. ............... 623/1.1 |
| 2004/0106976 A1 * | 6/2004 | Bailey et al. .............. 623/1.11 |
| 2004/0127981 A1 | 7/2004 | Rahdert et al. |
| 2004/0138745 A1 * | 7/2004 | Macoviak et al. ........... 623/2.36 |
| 2004/0206363 A1 * | 10/2004 | McCarthy et al. ............. 128/898 |
| 2004/0210303 A1 * | 10/2004 | Sedransk .................... 623/2.1 |
| 2004/0243170 A1 * | 12/2004 | Suresh et al. ................ 606/198 |

FOREIGN PATENT DOCUMENTS

WO WO 2003/028558 A2 4/2003
WO WO-2005/007036 A1 1/2005

OTHER PUBLICATIONS

The Merck Manual Online—Second Home Edition, Mitral Regurgitation, Merck, 2nd Edition, accessed on Apr. 2, 2008, posted Sep. 28, 2004, <http://web.archive.org/web/20040928074656/http://www.merck.com/mmhe/sec03/ch028/ch028b.html>.*

* cited by examiner

*Primary Examiner*—Corrine M McDermott
*Assistant Examiner*—Rebecca Straszheim
(74) *Attorney, Agent, or Firm*—Tarolli, Sundheim, Covell & Tummino LLP

(57) ABSTRACT

An apparatus for percutaneously replacing a diseased cardiac valve includes an expandable support member for positioning in an atrial chamber. The expandable support member includes at least one anchoring portion for anchoring in at least one opening that extends from the atrial chamber and a main body portion located adjacent the at least one anchoring portion. The main body portion has a cage-like structure and is adapted to conform to a size and shape of the atrial chamber. An expandable ring is selectively connected to the main body portion. The expandable ring is adapted to engage an annulus of the diseased cardiac valve. A prosthetic valve is attached to the expandable ring. The prosthetic valve is adapted to replace the diseased cardiac valve. A method for percutaneously replacing a diseased cardiac valve is also described.

16 Claims, 11 Drawing Sheets

PERCUTANEOUS ATRIOVENTRICULAR VALVE AND METHOD OF USE

RELATED APPLICATION

This application, U.S. patent application Ser. No. 11/509,469, filed Aug. 24, 2006, claims priority from U.S. Provisional Application Ser. No. 60/711,233, filed Aug. 25, 2005.

TECHNICAL FIELD

The present invention relates to an apparatus and method for replacing a cardiac valve, and is particularly directed to an apparatus and method for the correction of mitral and tricuspid valve disorders via a minimally invasive, percutaneous approach.

BACKGROUND OF THE INVENTION

There are two atrioventricular (AV) valves in the heart; one on the left side of the heart and one on the right side of the heart. The left side AV valve is the mitral valve and the right side AV valve is the tricuspid valve. Both of these valves are subject to damage and dysfunction requiring the valves to be repaired or replaced.

The mitral and tricuspid valves differ significantly in anatomy. While the annulus of the mitral valve is generally D-shaped, the annulus of the tricuspid valve is more circular. The effects of valvular dysfunction vary between the mitral and tricuspid valves. For example, mitral valve regurgitation has more severe physiological consequences to the patient than does tricuspid valve regurgitation, a small amount of which is tolerable.

In mitral valve insufficiency, the valve leaflets do not fully close and a certain amount of blood leaks back into the left atrium when the left ventricle contracts. As a result, the heart has to work harder by pumping not only the regular volume of blood, but also the extra volume of blood that is regurgitated back into the left atrium. The added workload creates an undue strain on the left ventricle, and this strain can eventually wear out the heart and result in morbidity. Consequently, proper function of the mitral valve is critical to the pumping efficiency of the heart.

Mitral and tricuspid valve disease is traditionally treated by either surgical repair with an annuloplasty ring or surgical replacement with a valve prosthesis. Surgical valve replacement or repair, however, is often an exacting operation. The operation requires the use of a heart-lung machine for external circulation of the blood as the heart is stopped and then opened during the surgical intervention. Once the heart is opened, the artificial cardiac valves and/or annuloplasty rings are sewed in under direct vision.

Surgical repair and/or replacement of the AV valves can expose patients, especially elderly patients, to many risks. A percutaneous repair or replacement procedure that could be performed under local anesthesia in the cardiac catheterization lab, rather than in cardiac surgery, could therefore offer tremendous benefits to these patients. Consequently, an apparatus for replacing a diseased AV valve using a minimally invasive, percutaneous approach would be very helpful in providing additional opportunities to treat patients with valvular insufficiency and/or end stage heart failure.

SUMMARY OF THE INVENTION

In an embodiment of the present invention, an apparatus for percutaneously replacing a diseased cardiac valve is described. The apparatus includes an expandable support member for positioning in an atrial chamber. The expandable support member includes at least one anchoring portion for anchoring in at least one opening that extends from the atrial chamber and a main body portion located adjacent the at least one anchoring portion. The main body portion has a cage-like structure and is adapted to conform to a size and shape of the atrial chamber. An expandable ring is selectively connected to the main body portion. The expandable ring is adapted to engage an annulus of the diseased cardiac valve. A prosthetic valve is attached to the expandable ring. The prosthetic valve is adapted to replace the diseased cardiac valve.

In an embodiment of the present invention, a method for percutaneously replacing a diseased cardiac valve is described. An apparatus is provided. The apparatus includes an expandable support member having at least one anchoring portion, a cage-like main body portion located adjacent the at least one anchoring portion, an expandable ring selectively connected to the main body portion, and a prosthetic valve attached to the expandable ring. The apparatus is introduced into a patient's vasculature. At least a portion of the apparatus is positioned within the patient's atrial chamber. The apparatus is deployed in the atrial chamber with the at least one anchoring portion of the expandable support member being anchored in an opening extending from the atrial chamber. The expandable ring of the expandable support member is positioned adjacent the annulus of the diseased cardiac valve. The expandable ring of the expandable support member is engaged with the annulus of the diseased cardiac valve to position the prosthetic valve of the apparatus within the annulus of the diseased cardiac valve.

In an embodiment of the present invention, a method for percutaneously replacing a diseased cardiac valve is described. At least one dimension of the diseased cardiac valve and an atrial chamber of a patient is determined. An apparatus is provided in response to the at least one determined dimension. The apparatus includes an expandable support member having at least one anchoring portion, a cage-like main body portion located adjacent the at least one anchoring portion, an expandable ring selectively connected to the main body portion, and a prosthetic valve operatively secured to the expandable ring. A first guidewire is inserted through the patient's vasculature and into the atrial chamber. A peelable catheter having longitudinally spaced proximal and distal end portions is provided, the distal end portion including a slit having a predetermined length. The peelable catheter is passed over the first guidewire and the distal end portion is positioned in the atrial chamber such that at least a portion of the slit is located in the atrial chamber. A second guidewire is inserted into the peelable catheter. A distal end of the second guidewire is passed out of the peelable catheter through the slit. The distal end of the second guidewire is passed through the diseased cardiac valve and into a ventricular chamber. The apparatus is attached to a proximal end of the second guidewire. The apparatus is introduced into a patient's vasculature. The apparatus is passed through the peelable catheter along the first guidewire. At least a portion of the apparatus is positioned within the atrial chamber. The second guidewire is actuated to remove at least a portion of the apparatus from the slit of the peelable catheter within the atrial chamber. The apparatus is deployed in the atrial chamber with the at least one anchoring portion of the expandable support member being anchored in an opening extending from the atrial chamber. The expandable ring of the expandable support member is positioned adjacent the annulus of the diseased cardiac valve. The expandable ring of the expandable support member is engaged with the annulus of the diseased cardiac valve to position the prosthetic valve of the apparatus within the annulus of the diseased cardiac valve.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

The present invention relates to an apparatus and method for replacing a cardiac valve, and is particularly directed to an apparatus and method for the correction of mitral and tricuspid valve disorders via a minimally invasive, percutaneous approach. As representative of the present invention, FIG. 1 illustrates an apparatus 10 for replacing a diseased cardiac valve 46 (FIG. 2), such as a mitral valve 36 or tricuspid valve 34.

Figure 2:
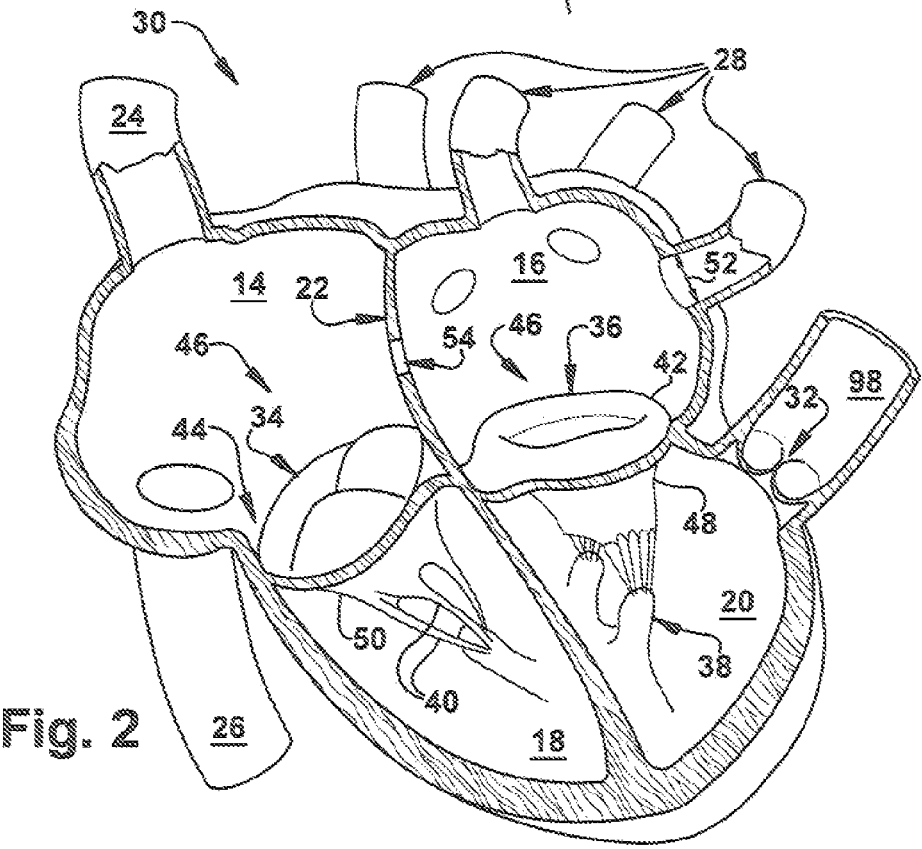
FIG. 2 is a cross-sectional schematic view of a human heart.

FIG. 2 schematically illustrates a human heart 30 which includes four chambers: the right and left atria 14 and 16, respectively, and the right and left ventricles 18 and 20, respectively. The right and left atria 14 and 16 are divided by the interatrial septum 22. The thin-walled right atrium 14 receives deoxygenated blood from the superior vena cava 24, the inferior vena cava 26, and from the coronary sinus (not shown). The thin-walled left atrium 16 receives oxygenated blood from pulmonary veins 28. The right and left ventricles 18 and 20 pump oxygenated and deoxygenated blood, respectively, throughout the body, and the pocket-like semilunar pulmonary valve (not shown) and aortic valve 32 prevent reflux into the ventricles. Atrial blood is pumped through the atrioventricular orifices, guarded by the tri-leaflet tricuspid valve 34 on the right side of the heart 30 and the bi-leaflet mitral valve 36 on the left side of the heart. The free edges of the leaflets 48 of the mitral valve 36 are attached to the papillary muscles 38 in the left and right ventricles 20 and 18 by chordae tendineae 40. The leaflets 48 of the mitral valve 36 extend across an annulus 42, which is an area of heart wall tissue at the junction of the atrial and ventricular walls that is relatively fibrous and significantly stronger than leaflet tissue. Similarly, the free edges of the leaflets 50 of the tricuspid valve 34 are attached to the papillary muscles 38 in the left and right ventricles 20 and 18 by chordae tendineae 40. The leaflets 50 of the tricuspid valve 34 extend across an annulus 44 at the junction of the atrial and ventricular walls.

Figure 1:
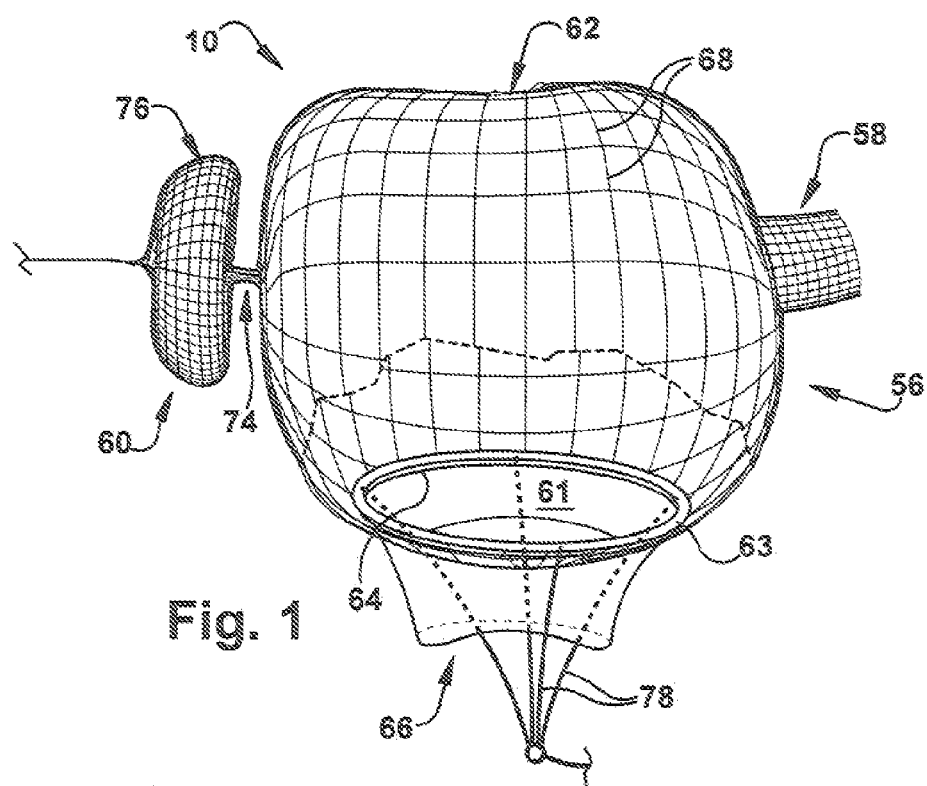
FIG. 1 is a perspective view showing an apparatus, in an expanded configuration, for replacing a diseased cardiac valve constructed in accordance with the present invention.
Figure 3:
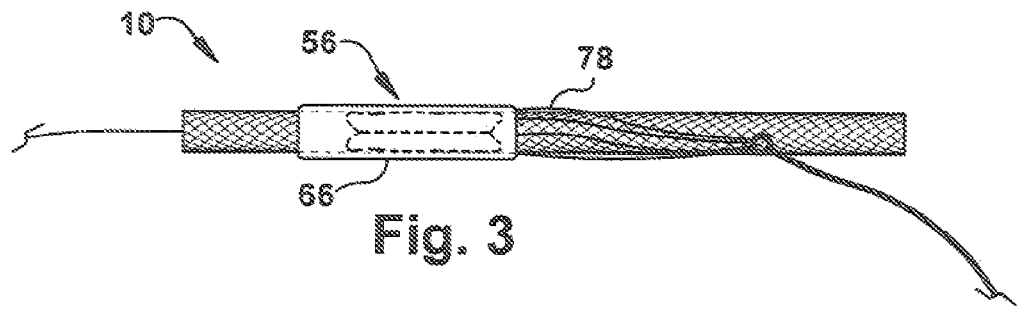
FIG. 3 is a cross-sectional view showing the apparatus of FIG. 1 in a collapsed configuration.

As shown in FIG. 1, one embodiment of the present invention includes an apparatus 10 for replacing a diseased mitral valve 36. The apparatus 10 comprises an expandable support member 56 having a non-tubular shape for percutaneously positioning in the left atrium 16. The expandable support member 56 includes at least a first anchoring portion 58 for anchoring in a first opening 52 (FIG. 2) that extends from the left atrium 16, an optional and oppositely disposed second anchoring portion 60 (FIG. 1; presumed to be present in the following discussion) for anchoring in a second opening 54 (FIG. 2) that extends from the left atrium, and a main body portion 62 (FIG. 1) intermediate the first and second anchoring portions having a cage-like structure for lining the left atrium. The apparatus 10 further comprises an expandable ring 64 attached to the main body portion 62 and a prosthetic valve 66 attached to the expandable ring. As illustrated in FIGS. 1 and 3, the apparatus 10 is moveable between an expanded configuration and a collapsed configuration, respectively.

Figure 4:
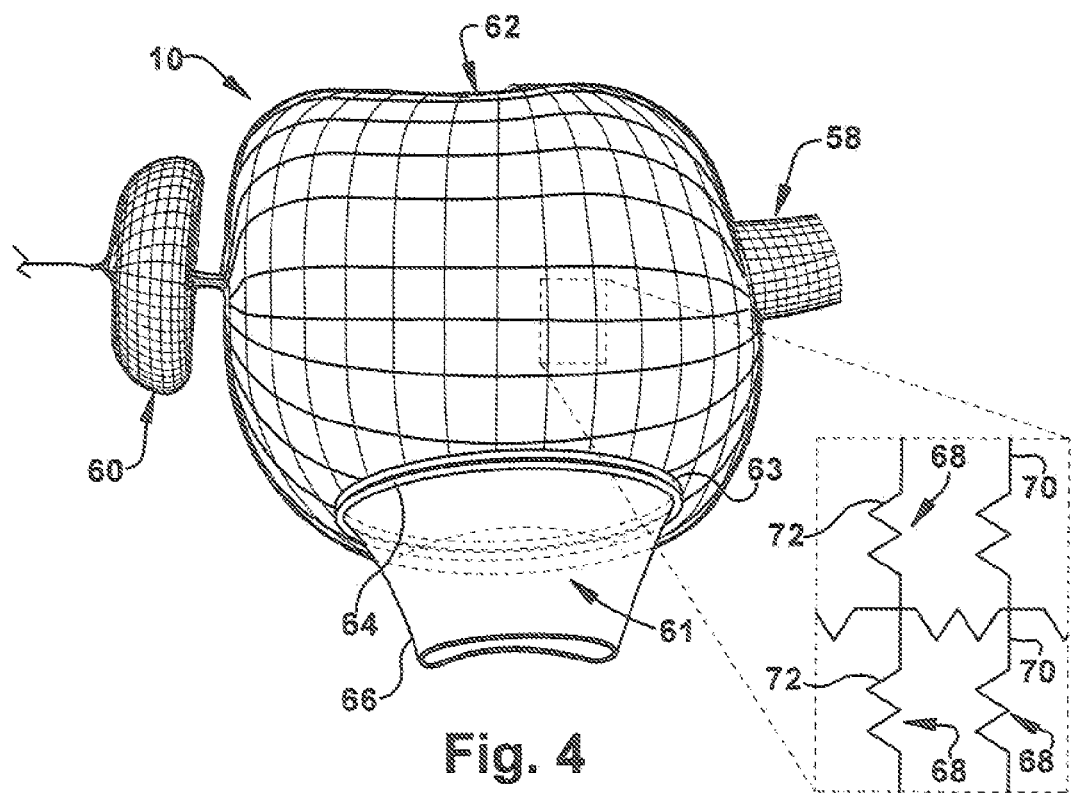
FIG. 4 is a perspective view showing strut members from an exploded portion of the apparatus of FIG. 1.

The main body portion 62 of the expandable support member 56 may be comprised of a plurality of strut members 68 having a three-dimensional cage-like structure for lining the left atrium 16. As illustrated in FIG. 4, the strut members 68 are comprised of linked straight segments 70 and curved segments 72 generally arranged in an alternating pattern. The straight and curved segments 70 and 72 may have pre-determined sizes and shapes. For example, the straight segments 70 may have a pre-determined size and shape that facilitates expansion of the apparatus 10. When the apparatus 10 is in an expanded configuration as shown in FIG. 4, the strut members 68 expand and acquire a previously determined size and shape so that the apparatus dynamically conforms to the size and shape of the left atrium 16. Additionally, when the apparatus 10 is configured as shown in FIG. 3, the straight and curved segments 70 and 72 are collapsed and folded. The main body portion 62 of the expandable support member 56 additionally includes an opening 61 defined by a generally circular ring member 63 at a lower (as viewed in the Figures) end of the main body portion.

The expandable support member 56 may be made from a biocompatible metallic or polymer material, or a metallic or polymer material that is suitably coated, impregnated, or otherwise treated with a material or combination of materials to impart biocompatibility. For instance, the expandable support member 56 may be made from a shape memory material such as Nitinol or a Nitinol alloy. Likewise, a polymer material may be injected into a different, base material forming the expandable support member 56 to impart desired stiffness, flexibility, resilience, or other properties. Additionally, the expandable support member 56 may be made from a biodegradable material including, for example, biopolymers such as thermoplastic starch, polyalctides, cellulose, and aliphatic aromatic copolyesters. The expandable support member 56 may also be made of a radio-opaque material or include radio-opaque markers to facilitate fluoroscopic visualization.

Moreover, the expandable support member 56 may be at least partially treated with at least one therapeutic agent for eluting into cardiac tissue or a cardiac chamber. The therapeutic agent is capable of preventing a variety of pathological conditions including, but not limited to, arrhythmias, thrombosis, stenosis and inflammation. Accordingly, the therapeutic agent may include at least one of an anti-arrhythmic agent, anticoagulant, an antioxidant, a fibrinolytic, a steroid, an anti-apoptotic agent, and/or an anti-inflammatory agent. Optionally or additionally, the therapeutic agent may be capable of treating or preventing other disease or disease processes such as microbial infections and heart failure. In these instances, the therapeutic agent may include an inotropic agent, a chronotropic agent, an anti-microbial agent, and/or a biological agent such as a cell or protein. A plurality of portions of the present invention may each be separately treated with a different one of the preceding therapeutic agents or other suitable therapeutic agents.

The first and second anchoring portions 58 and 60 of the apparatus 10 are respectively shaped to conform to the shape of the first and second openings 52 and 54. As shown in FIG. 1, the first anchoring portion 58 has a hollow, generally tubular shape and extends from the main body portion 62. The second anchoring portion 60 comprises a first section 74 and a second section 76. The first section 74 has a hollow, generally tubular shape and is intermediate the main body portion 62 and the second section 76. The second section 76 has a generally bulbous shape and extends from the first section 74.

The first and second anchoring portions 58 and 60 of the apparatus 10 have a cage-like structure which may differ from the cage-like structure of the main body portion 62. As illustrated in FIG. 1, the strut members 68 of the first and second anchoring portions 58 and 60 may be configured more densely as compared to the configuration of the strut members of the main body portion 62.

As shown in FIG. 1, the main body portion 62 includes only one of a second opening. The second opening is adapted to engage the ring member 63. The second opening has a diameter greater than the diameter of the first opening 52. The second opening is located substantially adjacent the annulus 42 (FIG. 2) of the diseased cardiac valve 46 when the apparatus 10 ( FIG. 1) is in the expanded configuration.

Figure 5:
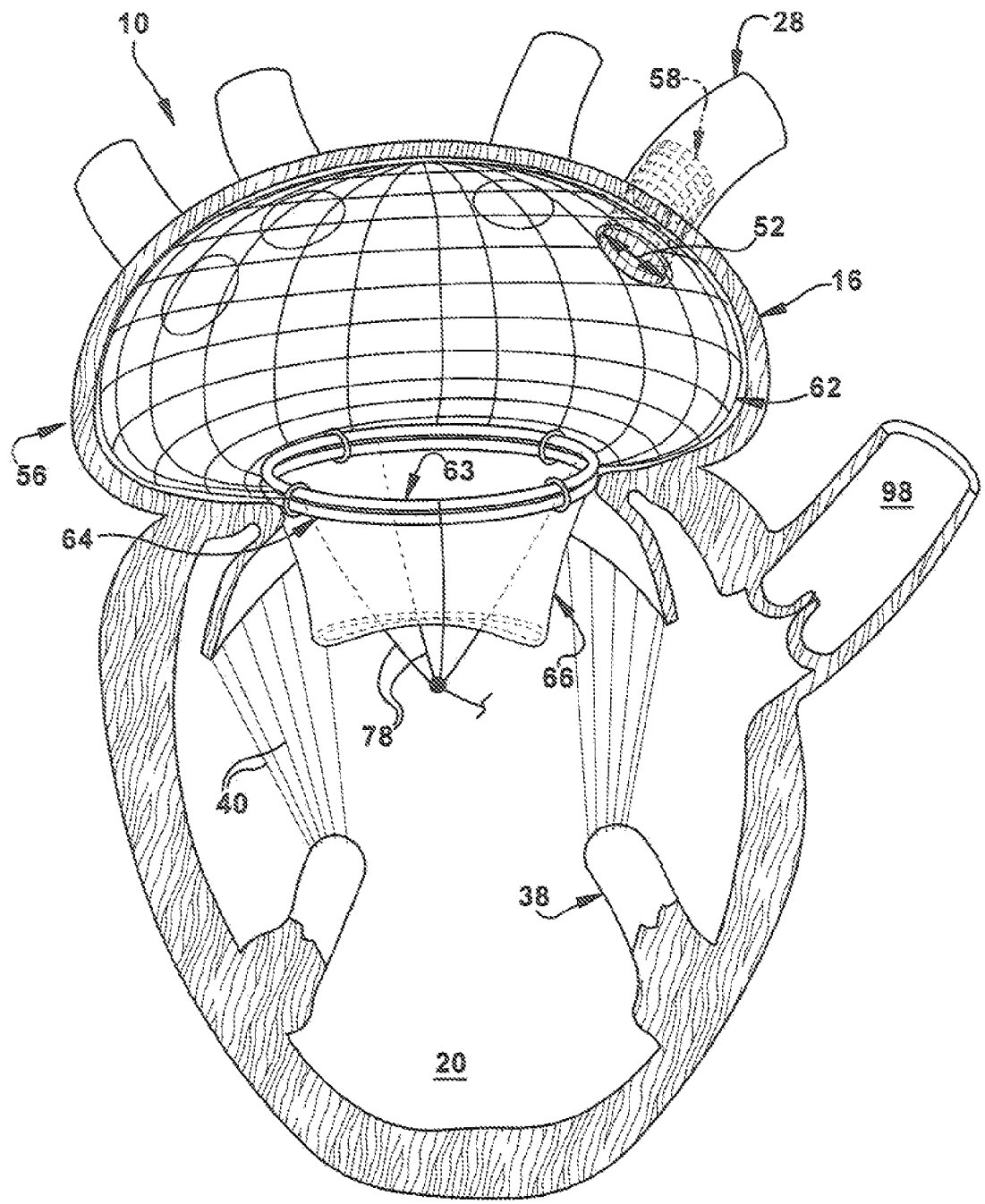
FIG. 5 is a cross-sectional view of a right portion of the human heart showing the apparatus of FIG. 1 secured in the mitral valve.
Figure 6:
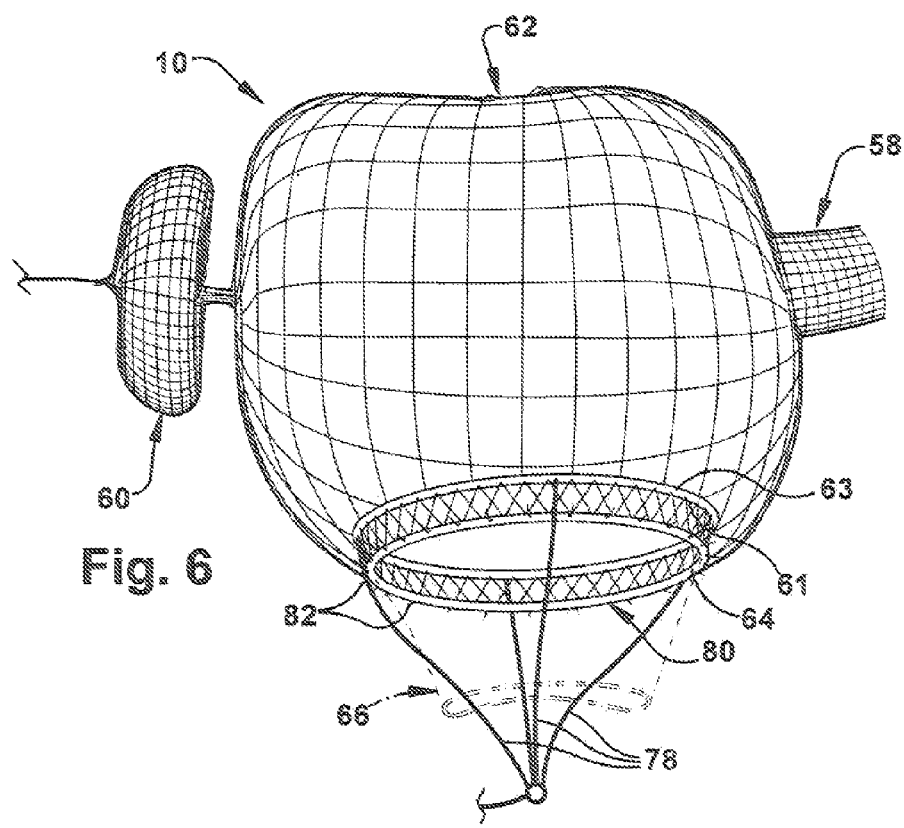
FIG. 6 is a perspective view showing an expandable ring attached to the apparatus in FIG. 1.

The expandable ring 64 of the apparatus 10 is operatively secured to the ring member 63 of the main body portion 62. As shown in FIG. 5, for example, suture loops may be used to secure the expandable ring 64 to the ring member 63. Alternatively, a biodegradable material (illustrated by the cross-hatched region in FIG. 6) may extend between the expandable ring 64 and the ring member 63 so that the expandable ring is operatively secured to the ring member. Examples of suitable biodegradable materials include biopolymers such as thermoplastic starch, polyalctides, cellulose, and aliphatic aromatic copolyesters.

The expandable ring 64 is operatively secured to the prosthetic valve 66 and is sutured to the prosthetic valve as known in the art. Alternatively, the prosthetic valve 66 may be secured to the expandable ring 64 in a variety of different manners including, for example, clips, pins, staples, and the like.

The expandable ring 64 has a semi-rigid or flexible structure, and may be made of a flexible, resiliently yieldable material such as silicone, plastic, polytetrafluoroethylene (PTFE), expanded-PTFE (ePTFE), polyurethane, or other similar material. A plurality of strands 78 are operatively attached to the expandable ring 64. The strands 78 extend from the expandable ring 64 for connection to a second catheter 99 to be described later. The strands 78 may be made of any biocompatible material including, for example, PTFE, ePTFE, or any other like material used with medical sutures.

Figure 6A:
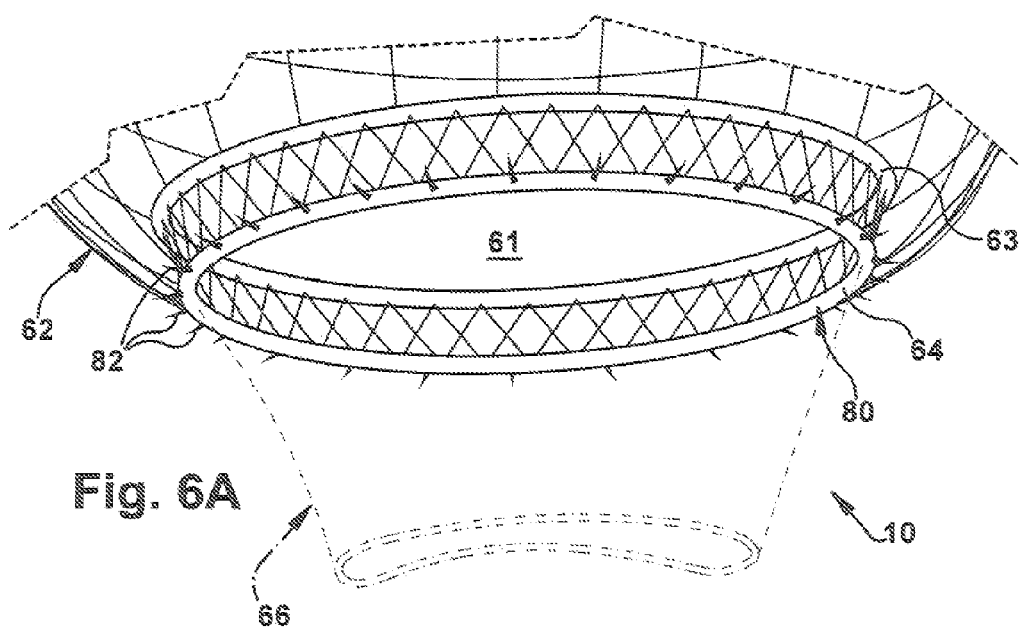
FIG. 6A is an exploded perspective view of the apparatus in FIG. 6 showing an attachment means of the expandable ring.

The expandable ring 64 may further comprise an attachment means 80 for attaching to the annulus 42 of the mitral valve 36. As shown in FIG. 6A, for example, the attachment means 80 can include a plurality of barbs 82 encased in a biodegradable material. Examples of suitable biodegradable materials include biopolymers such as thermoplastic starch, polyalctides, cellulose, and aliphatic aromatic copolyesters. Alternatively, the attachment means 80 can include adhesives, hooks, pins, clips, staples, and the like.

The prosthetic valve 66 of the present invention may be made from one or more pieces of biological material formed into a bi-leaflet conduit having dimensions that correspond to the dimensions of the diseased mitral valve 36. Materials of biological origin (e.g., bovine pericardial tissue, equine pericardial tissue, or bovine pericardial tissue) are typically used to construct prosthetic heart valves. Specific examples of such prosthetic heart valves are known in the art.

To replace a patient's mitral valve 36 using the apparatus 10, access to the left atrium 16 is achieved via a percutaneous approach. Once the left atrium 16 has been accessed, the dimensions of both the mitral valve 36 and the left atrium are determined. Various devices and methods for determining the dimensions of a cardiac valve 46 and an atrial chamber are known in the art.

After determining the dimensions of the mitral valve 36 and the left atrium 16, an appropriately-sized apparatus 10 for replacement of the mitral valve is selected. More particularly, the selected apparatus 10 will have an appropriately-sized expandable support member 56 and expandable ring 64, along with a prosthetic valve 66 appropriately dimensioned to the size and shape of the mitral valve 36.

Figure 7:
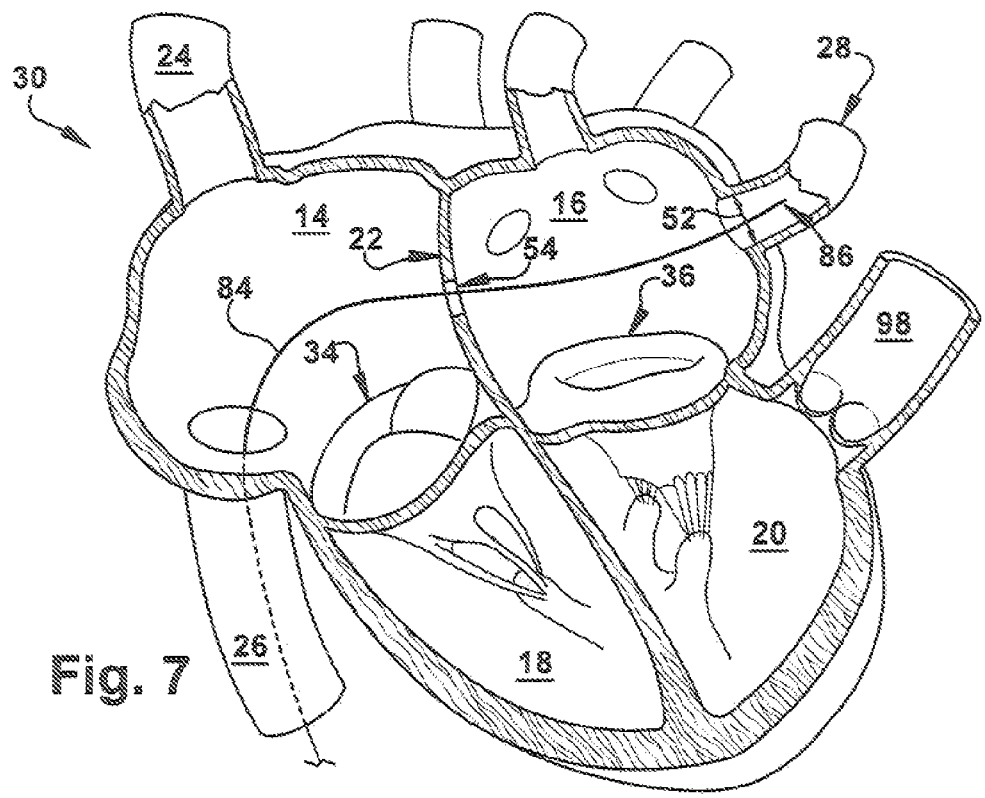
FIG. 7 is a cross-sectional view showing a first guidewire extending trans-septally through the human heart.

Next, a first guidewire 84 is inserted into a femoral vein (not shown) or jugular vein (not shown) and, under image guidance (e.g., fluoroscopy, ultrasound, magnetic resonance, computed tomography, or combinations thereof), respectively steered through the patient's vasculature into the inferior vena cava 26 or superior vena cava 24. The first guidewire 84 is then passed across the right atrium 14 so that the distal end 86 of the first guidewire pierces the interatrial septum 22 as shown in FIG. 7. The first guidewire 84 is then extended across the left atrium 16 and into a pulmonary vein 28 so that the distal end 86 of the first guidewire is securely positioned in the pulmonary vein.

Figure 8:
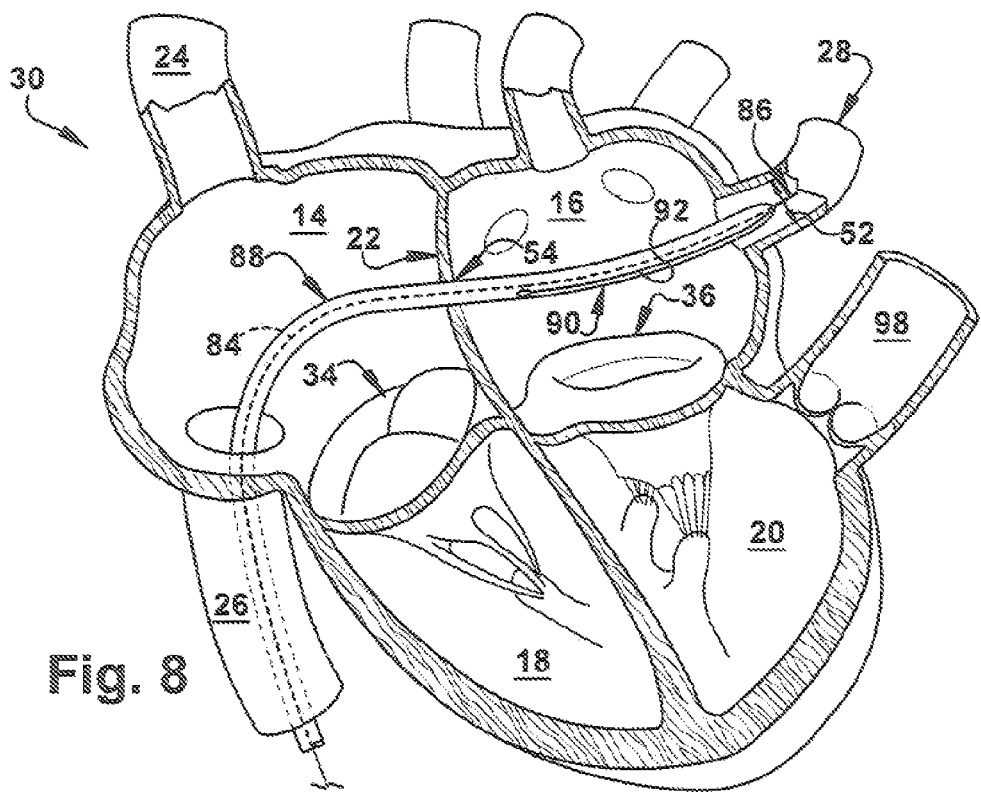
FIG. 8 is a cross-sectional view showing a peelable catheter advanced over the first guidewire.

After the first guidewire 84 is passed into the pulmonary vein 28, a peelable catheter 88 is passed over the first guidewire as shown in FIG. 8. A distal end portion 90 of the peelable catheter 88 contains a slit 92 having a pre-determined length. The peelable catheter 88 may be comprised of a flexible, resiliently yieldable material such as silicone, PTFE, ePTFE, plastic polymer, or the like.

Figure 9:
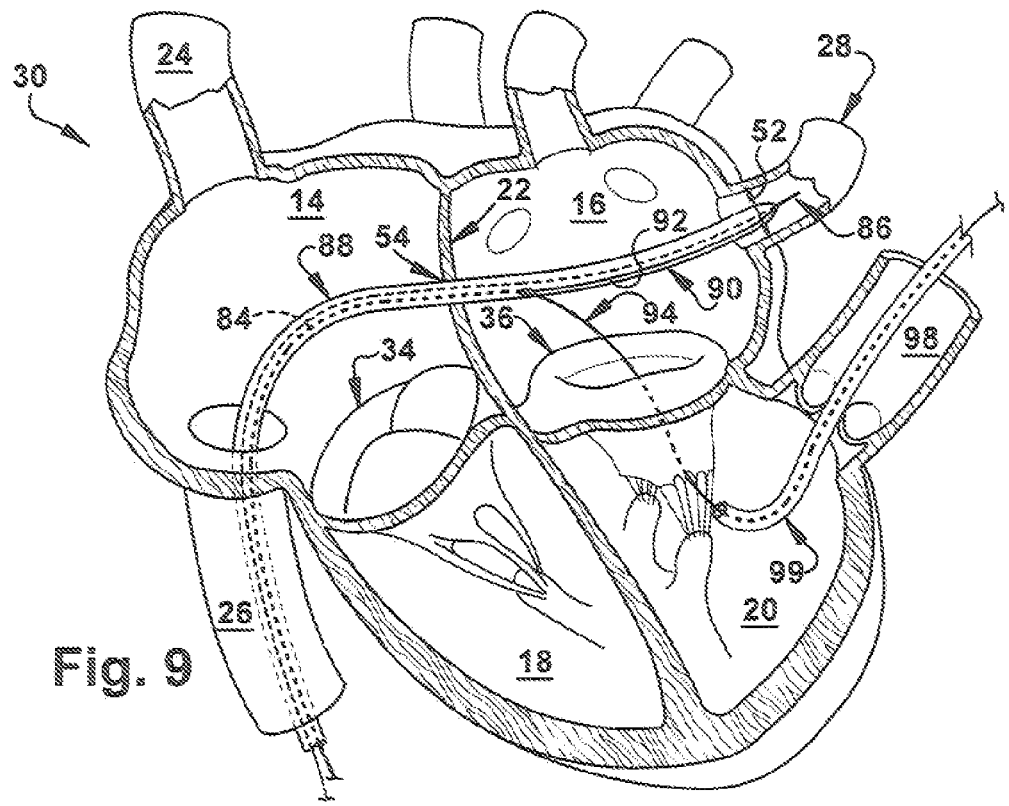
FIG. 9 is a cross-sectional view showing a second guidewire extending through the mitral valve and the ascending aorta.

Next, a second guidewire 94 is urged through the peelable catheter 88. As shown in FIG. 9, the second guidewire 94 is moved downward upon reaching the slit 92 of the peelable catheter 88 and then passed through the mitral valve 36 into the left ventricle 20. Thereafter, the second guidewire 94 is steered through the ascending aorta 98 to a location (not shown) where the second guidewire exits the patient's vasculature via the femoral artery.

Figure 10:
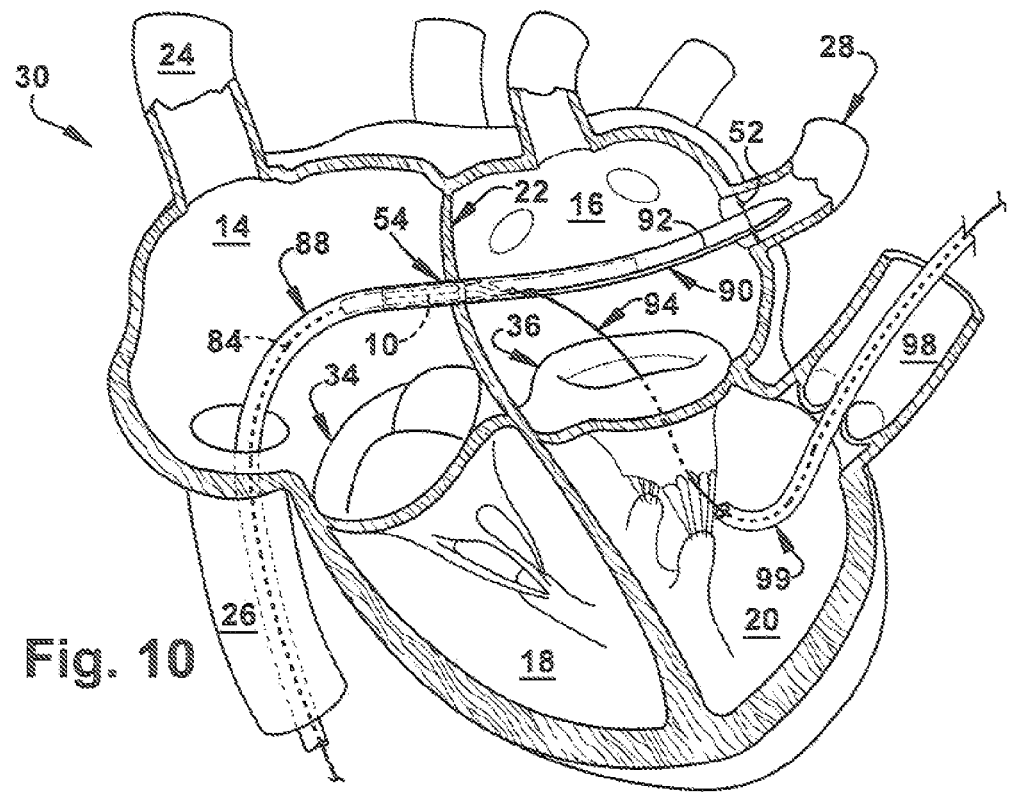
FIG. 10 is a cross-sectional view showing the apparatus of FIG. 3 contained in the peelable catheter.
Figure 11:
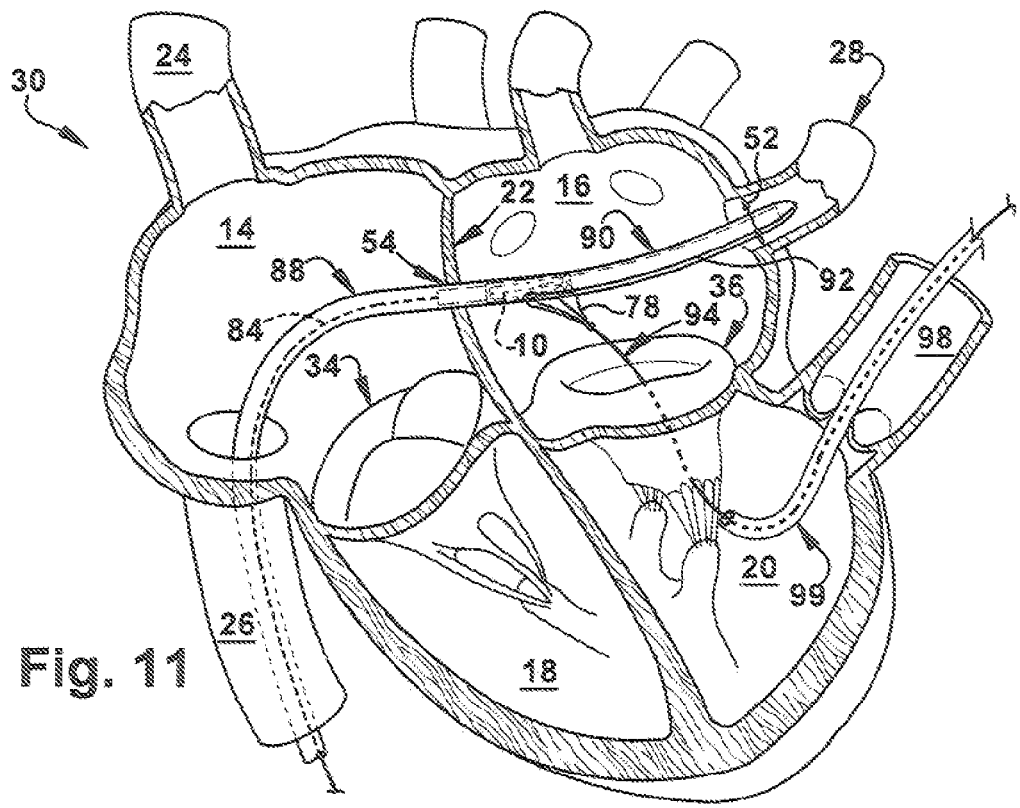
FIG. 11 is a cross-sectional view showing the apparatus of FIG. 3 being pulled downward through a slit in the peelable catheter.
Figure 12:
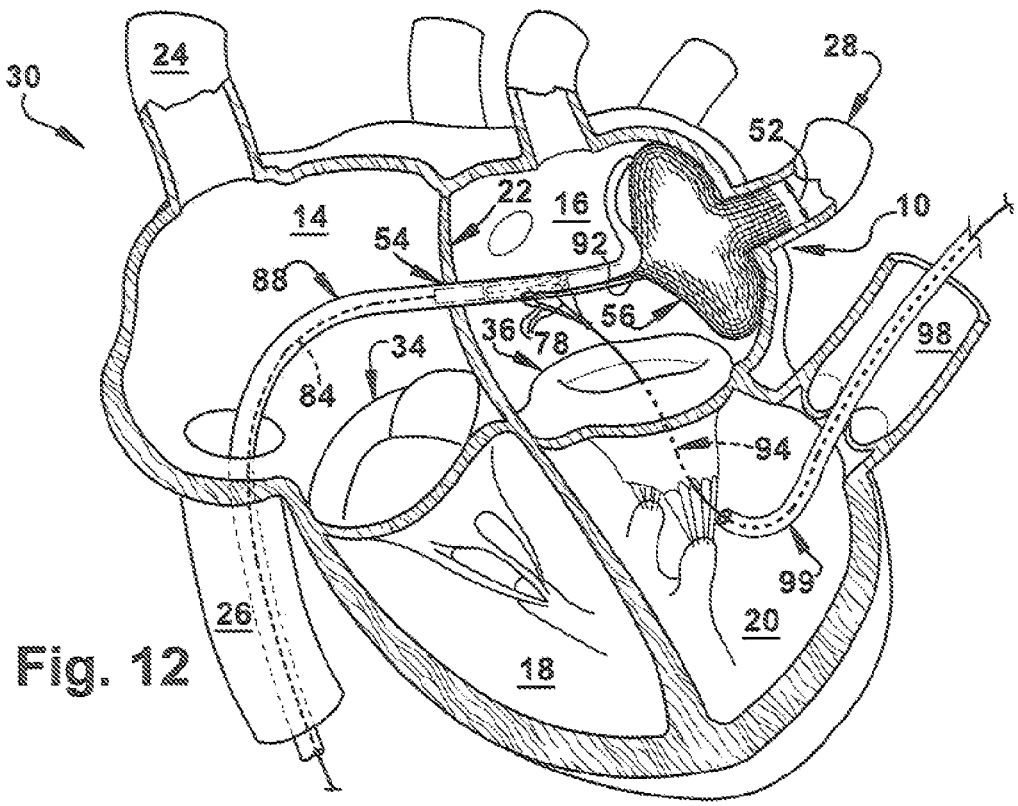
FIG. 12 is a cross-sectional view showing a first anchoring portion of the apparatus in FIG. 1 anchored in the pulmonary vein, and a main body portion partly deployed in a left atrium of the human heart.

Next, the apparatus 10, in its collapsed configuration, is attached to a proximal end (not shown) of the second guidewire 94, and a pushrod (not shown) or other similar device is then used to urge the apparatus along the first guidewire 84 into the left atrium 16 (FIG. 10). When the apparatus 10 is positioned near the slit 92 of the peelable catheter 88, the second guidewire 94 is pulled so that the strands 78 are pulled downward as shown in FIG. 11. The second guidewire 94 is then pulled so that the apparatus 10 is progressively freed from the peelable catheter 88 (FIG. 12).

Figure 13:
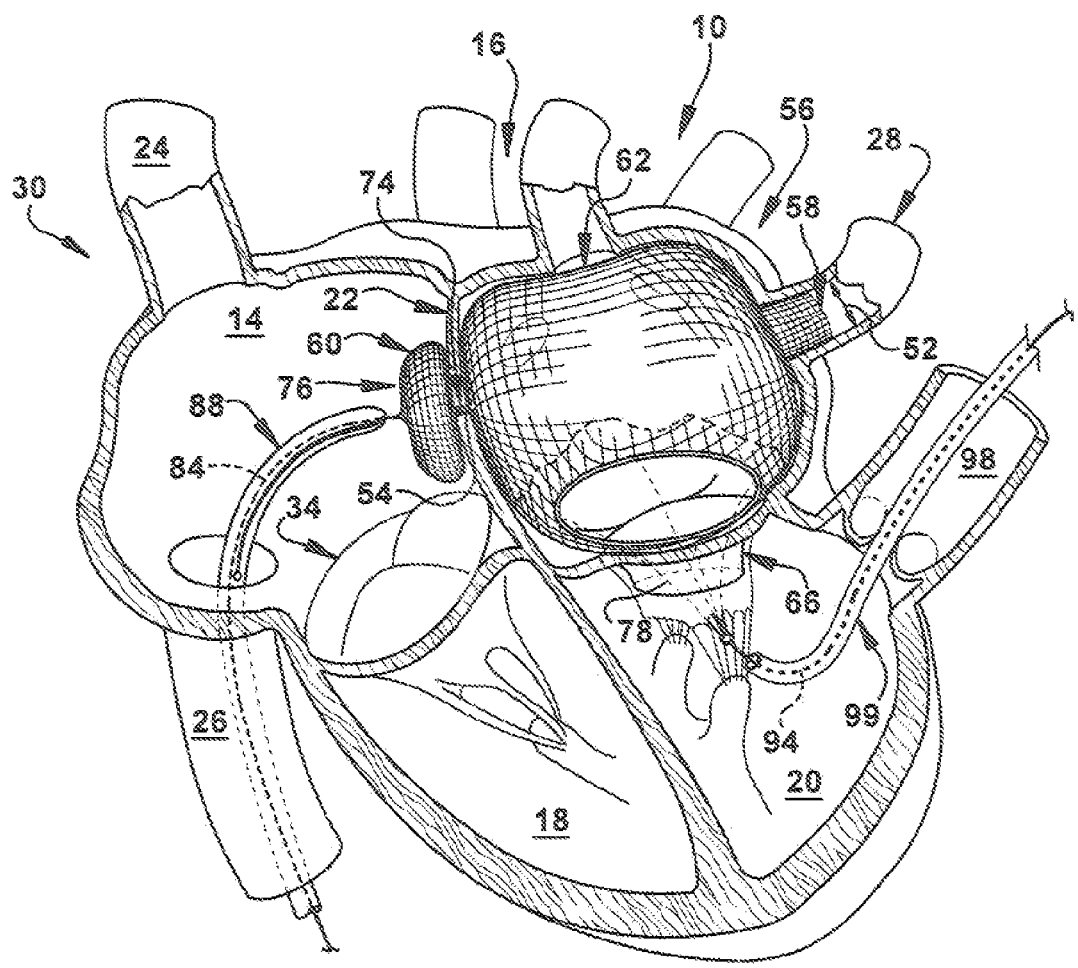
FIG. 13 is a cross-sectional view of the apparatus in FIG. 1 deployed in the left atrium of the human heart.

As the apparatus 10 is progressively freed from the peelable catheter 88, the first anchoring portion 58 expands into the pulmonary vein 28 or another left atrium 16 appendage and is securely anchored therein. The main body portion 62 of the apparatus 10 then expands into the left atrium 16 so that the first section 74 of the second anchoring portion 60, when present, is secured within the interatrial septum 22 as shown in FIG. 13. The second section 76 of the second anchoring portion is then expanded adjacent the interatrial septum 22 as shown in FIG. 13. With the first and second anchoring portions 58 and 60 expanded as shown in FIG. 13, the expandable support member 56 is prevented from rocking in the left atrium 16.

The expandable ring 64 of the apparatus 10 is simultaneously positioned adjacent the mitral valve 36 as the expandable support member 56 is deployed in the left atrium 16. The expandable ring 64 is further positioned in the annulus 42 of the mitral valve 36 by pulling the second guidewire 94 and thus tensioning the strands 78. As shown in FIG. 13, tensioning of the strands 78 pulls the expandable ring 64 downward into the annulus 42 of the mitral valve 36, in turn causing the prosthetic valve 66 to move into the position of the native mitral valve and displace the mitral valve leaflets 48.

After the prosthetic valve 66 is positioned in the annulus 42 of the native mitral valve 36, the attachment means 80 affixes the expandable ring 64 to the annulus. For example, in the embodiment of FIG. 6A where the attachment means 80 comprises a plurality of barbs 82 encased in a biodegradable material, the biodegradable material degrades over a period of 1-3 days and consequently exposes the barbs so that the barbs penetrate into the annulus 42 of the mitral valve 36 and affix the expandable ring 64 to the annulus.

Figure 14:
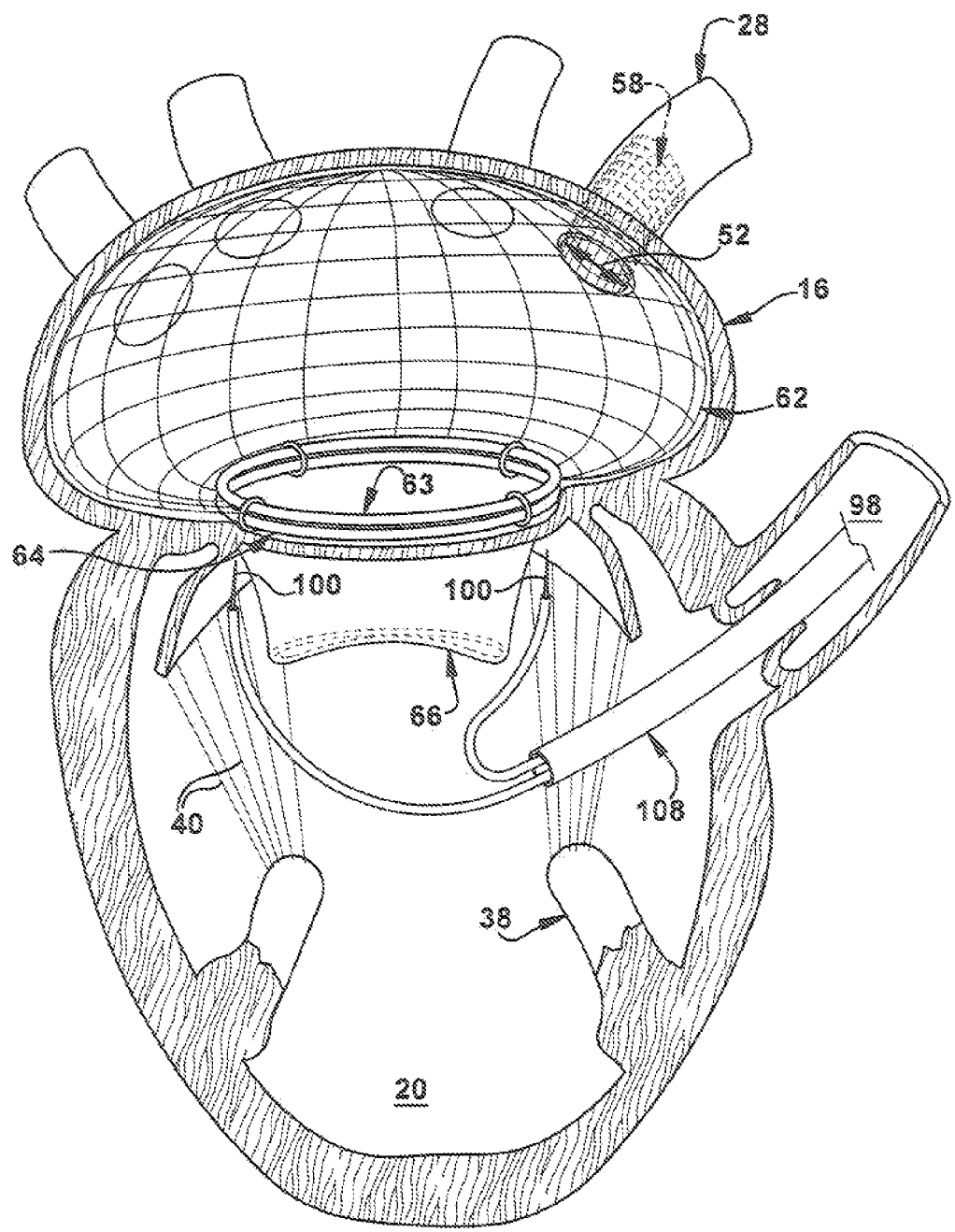
FIG. 14 is a cross-sectional view of a right portion of the human heart showing microneedles being used to secure the apparatus of FIG. 1 to the mitral valve.

Alternatively, the prosthetic valve 66 may be attached to the annulus 42 of the mitral valve 36 using microneedles 100 as shown in FIG. 14. The microneedles 100 may be inserted in a retrograde fashion through a catheter 108 and then used to suture the expandable ring 64 to the annulus 42 of the mitral valve 36. Other means for attaching the prosthetic valve 66 to the annulus 42 of the mitral valve 36 may include adhesives, clips, staples, pins, and the like.

After affixing the expandable ring 64 to the annulus 42 of the mitral valve 36, catheters 88 and 99 and the first and second guidewires 84 and 94 may be removed.

After a certain amount of time following implantation of the apparatus 10, it may be desirable to remove the main body portion 62 of the apparatus from the left atrium 16. For instance, in the embodiment of FIG. 5 in which the ring member 63 is attached to the expandable ring 64 by suture loops, the suture loops may be severed and the apparatus 10 collapsed so that the main body portion 62 can be removed from the left atrium 16. Alternatively, where the expandable ring 64 and the ring member 63 are attached via a biodegradable material, the biodegradable material may degrade over a period of several weeks, in turn causing the main body portion 62 to detach from the prosthetic valve 66 and allow removal of the main body portion from the left atrium 16.

It may also be desirable to complete the operation and not extract the main body portion 62. For example, the main body portion 62 may remain in the left atrium 16 and become endothelialized (e.g., by endocardial endothelial cells). Alternatively, where the implanted expandable support member 56 is made of a biodegradable material, the expandable support member may remain in the left atrium 16 and safely degrade over a period of several months. Significantly, the use of a biodegradable expandable support member 56 may reduce or eliminate the risk of thrombogenesis.

In another embodiment of the present invention, an apparatus $10_a$ for replacing a diseased tricuspid valve 34 is provided. The apparatus $10_a$ is identically constructed as the apparatus 10 shown in FIG. 1, except where as described below. In FIGS. 15-18, structures that are identical as structures in FIG. 1 use the same reference numbers, whereas structures that are similar but not identical carry the suffix "a".

Figure 15:
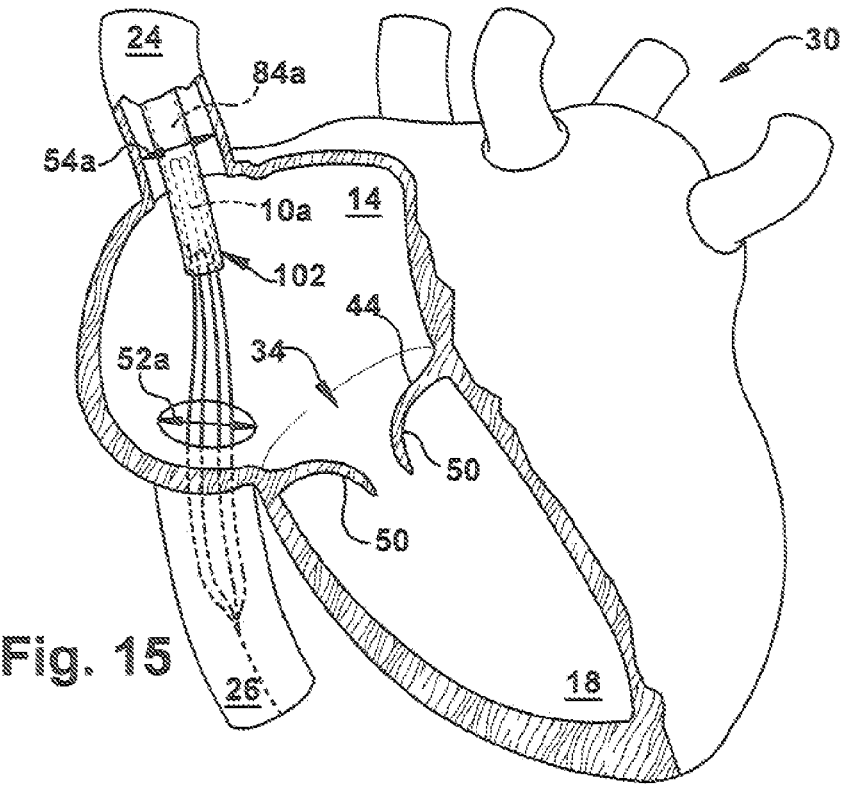
FIG. 15 is a cross-sectional view showing an alternate embodiment of the apparatus of FIG. 1 in a collapsed configuration extending into the right atrium of the human heart.
Figure 16:
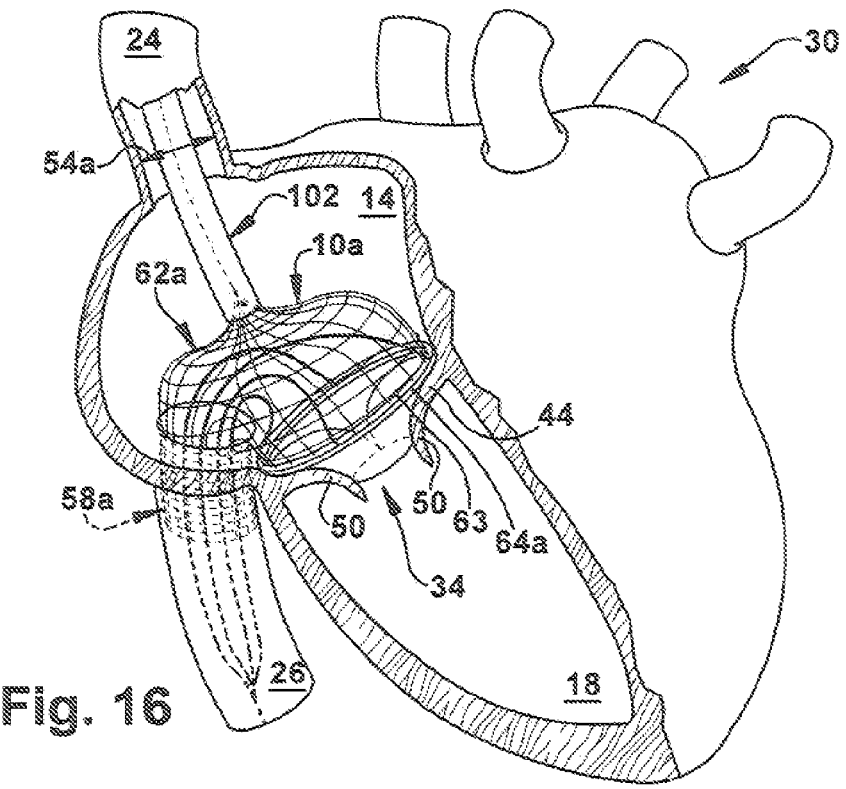
FIG. 16 is a cross-sectional view showing a first anchoring portion of the apparatus in FIG. 15 anchored in the inferior vena cava, and a main body portion of the apparatus partly deployed in the right atrium.
Figure 18:
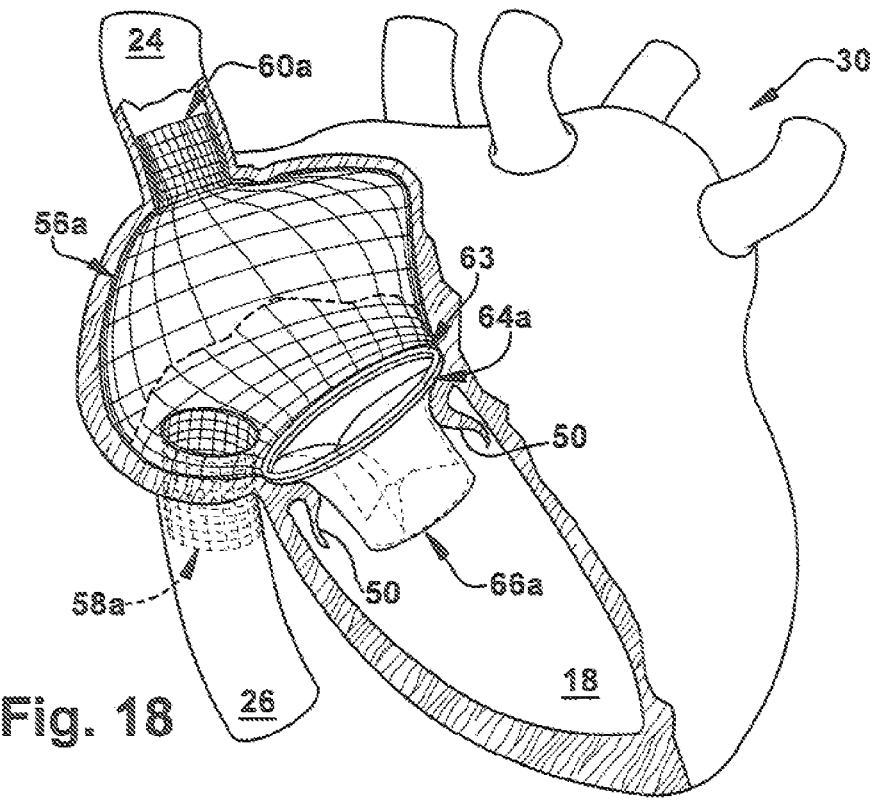
FIG. 18 is a cross-sectional view showing the apparatus of FIG. 15 deployed in the right atrium of the human heart.

The apparatus $10_a$ comprises an expandable support member $56_a$ for percutaneously positioning in the right atrium 14. The expandable support member $56_a$ includes a first anchoring portion $58_a$ for anchoring in a first opening $52_a$ that extends from the right atrium 14, an oppositely disposed second anchoring portion $60_a$ for anchoring in a second opening $54_a$ that extends from the right atrium, and a main body portion $62_a$ intermediate the first and second anchoring portions having a cage-like structure for lining the right atrium. The apparatus $10_a$ further comprises an expandable ring $64_a$ attached to the main body portion $62_a$ and a prosthetic valve $66_a$ attached to the expandable ring. As illustrated in FIGS. 15 and 18, the apparatus $10_a$ is moveable between an expanded configuration and a collapsed configuration, respectively.

Figure 17:
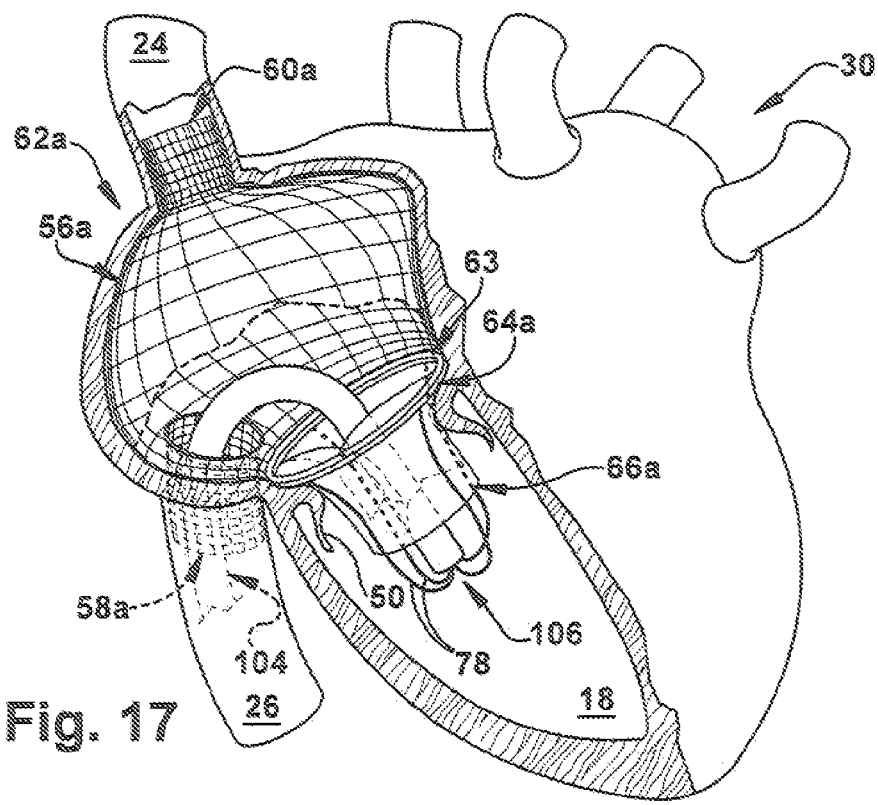
FIG. 17 is a cross-sectional view showing a second catheter extending through the inferior vena cava and into the tricuspid valve so that a prosthetic valve of the apparatus in FIG. 15 replaces the tricuspid valve.

As shown in FIG. 17, the second anchoring portion $60_a$ of the apparatus $10_a$ is shaped to conform to the shape of the second opening $54_a$ extending from the right atrium 14. More particularly, the second anchoring portion $60_a$ has a hollow, generally tubular shape and extends from the main body portion $62_a$. The second anchoring portion $60_a$ has a cage-like structure which may differ from the cage-like structure of the main body portion $62_a$. As illustrated in FIG. 17, the strut members 68 of the second anchoring portion $60_a$ may be configured more densely as compared to the configuration of the strut members of the main body portion $62_a$.

The expandable ring $64_a$ of the apparatus $10_a$ is attached to the prosthetic valve $66_a$ and is suitably adapted to conform to the shape of the annulus 44 of the tricuspid valve 34. The prosthetic valve $66_a$ may be made from one or more pieces of biological material formed into a tri-leaflet conduit having dimensions that correspond to the dimensions of the diseased tricuspid valve 34. Materials of biological origin (e.g., bovine pericardial tissue, equine pericardial tissue, or bovine pericardial tissue) are typically used to construct prosthetic heart valves. Specific examples of such prosthetic heart valves are known in the art.

To replace a patient's tricuspid valve 34 using the apparatus $10_a$, access to the right atrium 14 is achieved via a percutaneous approach. Once the right atrium 14 has been accessed, the dimensions of both the tricuspid valve 34 and the right atrium are determined. Various devices and methods for determining the dimensions of a cardiac valve 46 and an atrial chamber are known in the art.

After determining the dimensions of the tricuspid valve 34 and the right atrium 14, an appropriately-sized apparatus 10$_a$ for replacement of the tricuspid valve is selected. More particularly, the selected apparatus 10$_a$ will have an appropriately-sized expandable support member 56$_a$ and expandable ring 64$_a$, along with a prosthetic valve 66$_a$ appropriately dimensioned to the size and shape of the tricuspid valve 34.

Next, a first guidewire 84$_a$ is inserted into the patient's jugular vein (not shown) and, under image guidance (e.g., fluoroscopy, ultrasound, magnetic resonance, computed tomography, or combinations thereof), steered through the superior vena cava 24 into the right atrium 14. Once the first guidewire 84$_a$ is delivered to the right atrium 14, a first catheter 102 is passed over the first guidewire and advanced into the right atrium. The apparatus 10$_a$, in its collapsed configuration, is then attached to a proximal end (not shown) of the first guidewire 84$_a$ and urged into the right atrium 14 so that strands 78 extend downwardly through the right atrium and into the inferior vena cava 26 as shown in FIG. 15.

As illustrated in FIG. 15, the apparatus 10$_a$ is then progressively freed from the first catheter 102 so that the first anchoring portion 58$_a$ expands into the inferior vena cava 26 and is securely anchored therein. The first catheter 102 is then withdrawn from the right atrium 14 so that the main body portion 62$_a$ of the apparatus 10$_a$ expands to line the right atrium. The second anchoring portion 60$_a$ then extends into the superior vena cava 24 do that the second anchoring portion is securely anchored therein. It is contemplated that the apparatus 10$_a$ could be suitably anchored using either one of the first and second anchoring portions 58$_a$ and 60$_a$ singly or both together, as desired.

The expandable ring 64$_a$ of the apparatus 10$_a$ is simultaneously positioned adjacent the tricuspid valve 34 as the expandable support member 56$_a$ is deployed in the right atrium 14. The expandable ring 64$_a$ is further positioned in the annulus 44 of the tricuspid valve 34 via a second catheter 104. More particularly, the second catheter 104 is inserted into a femoral vein (not shown) and then urged through the femoral vein into the inferior vena cava 26. As the second catheter 104 is urged through the inferior vena cava 26, a distal end 106 of the second catheter 104 operatively captures the strands 78 of the apparatus 10$_a$. The second catheter 104 is then retroflexed as shown in FIG. 17 so that the distal end 106 extends into the prosthetic valve 66$_a$. The second catheter 104 is next urged downward through the prosthetic valve 66$_a$ so that the rigid or semi-rigid structure of the second catheter tensions the strands 78. The expandable ring 64$_a$ is then pulled downward toward the tricuspid valve 34, and the prosthetic valve 66$_a$ moves into the position of the native tricuspid valve and displaces the tricuspid valve leaflets 50 as shown in FIG. 18.

After the prosthetic valve 66$_a$ is positioned in the annulus 44 of the native tricuspid valve 34, the attachment means 80 affixes the expandable ring 64$_a$ to the annulus. For example, where the attachment means 80 comprises a plurality of barbs 82 encased in a biodegradable material, the biodegradable material degrades over a period of 1-3 days and consequently exposes the barbs so that the barbs penetrate into the annulus 44 of the tricuspid valve 34 and affix the expandable ring 64$_a$ to the annulus.

Alternatively, the prosthetic valve 66$_a$ may be attached to the annulus 44 of the tricuspid valve 34 using microneedles 100. The microneedles 100 may be inserted through the pulmonary artery (not shown) via a catheter 108 and then used to suture the expandable ring 64$_a$ to the annulus 44 of the tricuspid valve 34. Other means for attaching the prosthetic valve 66$_a$ to the annulus 44 of the tricuspid valve 34 may include adhesives, clips, staples, pins, and the like.

After affixing the expandable ring 64$_a$ to the annulus 44 of the tricuspid valve 34, catheters 102 and 104 and the first guidewire 84$_a$ may be removed.

After a certain amount of time following implantation of the apparatus 10$_a$, it may be desirable to remove the main body portion 62$_a$ of the apparatus from the right atrium 14. For example, where the ring member 63 is attached to the expandable ring 64$_a$ by suture loops, the suture loops may be severed and the apparatus 10$_a$ collapsed so that the main body portion 62$_a$ can be removed from the right atrium 14. Alternatively, where the expandable ring 64$_a$ and the ring member 63 are attached via a biodegradable material, the biodegradable material may degrade over a period of 1-2 weeks, in turn causing the main body portion 62$_a$ to detach from the prosthetic valve 66$_a$ and allow removal of the main body portion from the right atrium 14.

It may also be desirable to complete the operation and not extract the main body portion 62$_a$. For example, the main body portion 62$_a$ may remain in the right atrium 14 and become endothelialized (e.g., by endocardial endothelial cells). Alternatively, where the implanted expandable support member 56$_a$ is made of a biodegradable material, the expandable support member may remain in the right atrium 14 and safely degrade over a period of 3-6 months. Significantly, the use of a biodegradable expandable support member 56$_a$ may reduce or eliminate the risk of thrombogenesis.

From the above description of the invention, those skilled in the art will perceive improvements, changes and modifications. The skilled artisan should appreciate that a transthoracic approach may be used to replace a diseased cardiac valve 46 by, for example, creating a port or hole in an atrial chamber and then delivering the present invention therethrough. Any number of anchoring portions could be provided and configured to anchor in any suitable openings extending from the atrial chamber being lined. Such improvements, changes and modifications within the skill of the art are intended to be covered by the appended claims.

Having described the invention, we claim:

1. An apparatus for percutaneously replacing a diseased cardiac valve, the apparatus being movable between an expanded configuration and a collapsed configuration, the apparatus comprising:

an expandable support member for positioning in an atrial chamber, the expandable support member including a main body portion having a non-tubular cage-like structure configured to line the atrial chamber in the expanded configuration, and one of a first opening which in the expanded configuration is located substantially adjacent the annulus of the diseased cardiac valve;

at least one anchoring having a tubular configuration extending from the main body portion and being adapted to conform to the shape of a second opening that extends from the atrial chamber, where the junction formed by the main body portion and the at least one anchoring portion defines a third opening, which is smaller than the first opening;

a ring member adapted to engage the first opening of the main body portion;

an expandable ring operatively secured to the ring member; and a prosthetic valve attached to the expandable ring, the prosthetic valve being adapted to replace the diseased cardiac valve.

2. The apparatus of claim 1, wherein at least a portion of the apparatus is formed from a biodegradable material.

3. The apparatus of claim 1, wherein at least a portion of the apparatus is adapted to elute a therapeutic agent.

4. The apparatus of claim 1, wherein the prosthetic valve is attachable to the annulus of the diseased cardiac valve.

5. The apparatus of claim 4, wherein the expandable ring includes a plurality of barbs at least partially encased in a biodegradable material.

6. The apparatus of claim 1, wherein at least one anchoring portion is the second anchoring portion for anchoring in a first opening that extends from the atrial chamber, and an oppositely disposed second anchoring portion is provided for anchoring in a fourth opening that extends from the atrial chamber, the main body portion being intermediate the first and second anchoring portions.

7. The apparatus of claim 1, wherein the expandable ring is adapted to support the prosthetic valve in the annulus of the diseased cardiac valve when the main body portion is detached from the expandable ring.

8. The apparatus of claim 1, wherein the main body portion includes a plurality of strut members having a three-dimensional cage-like structure.

9. The apparatus of claim 1, wherein the at least one anchoring portion has a cage-like structure, the cage-like structure of the at least one anchoring portion having a different configuration from the cage-like structure of the main body portion.

10. The apparatus of claim 1, wherein a biodegradable material extends between the expandable ring and the ring member, the biodegradable material being adapted to release the expandable ring from the ring member after a predetermined time has elapsed.

11. The apparatus of claim 1, wherein the ring member is located between the main body portion and the first opening.

12. The apparatus of claim 1, wherein the prosthetic valve extends below the first opening, opposite the main body portion.

13. The apparatus of claim 1, wherein the ring member and the expandable ring are axially aligned with respect to the first opening.

14. The apparatus of claim 1 further including a plurality of strands that are attached to and extend from the expandable ring.

15. An apparatus for percutaneously replacing a diseased mitral valve, the apparatus being movable between an expanded configuration and a collapsed configuration, the apparatus comprising:

an expandable support member for positioning in the left atrial chamber, the expandable support member including at least one anchoring portion for anchoring in a pulmonary vein, a second anchoring portion for anchoring across the interatrial septum, and a main body portion located intermediate the at least one anchoring portion and the second anchoring portion, each of the at least one anchoring portion and the second anchoring portion extending from the main body portion, the main body portion having a cage-like structure and being adapted to conform to a size and shape of the left atrial chamber;

a ring member connected to the main body portion;

an expandable ring operatively secured to the ring member; and a prosthetic valve attached to the expandable ring, the prosthetic valve being adapted to replace the diseased mitral valve;

wherein the junction formed by the main body portion and the at least one anchoring portion defines a first opening;

wherein the main body portion includes only one of a second opening defined by the ring member, the second opening having a diameter greater than the diameter of the first opening and being located substantially adjacent the annulus of the diseased mitral valve when the apparatus is in the expanded configuration;

wherein the second anchoring portion comprises a first section and a second section, the first section having a hollow, tubular shape and being intermediate the main body portion and the second section, the second section having a bulbous shape and extending from the first section.

16. An apparatus for percutaneously replacing a diseased tricuspid valve, the apparatus being movable between an expanded configuration and a collapsed configuration, the apparatus comprising:

an expandable support member for positioning in the right atrium, the expandable support member including a main body portion having a non-tubular cage-like structure configured to line the right atrium in the expanded configuration, and only one of a first opening which in the expanded configuration is located substantially adjacent the annulus of the diseased tricuspid valve;

a first anchoring portion oppositely disposed from a second anchoring portion, each of the first and second anchoring portions having a tubular configuration and extending from the main body portion and being adapted to conform to the shape of the superior vena cava and the inferior vena cava, respectively, where the junctions formed by the main body portion and the first and second anchoring portions respectively define second and third openings which are smaller than the first opening;

a ring member adapted to engage the first opening of the main body portion;

an expandable ring operatively secured to the ring member; and a prosthetic valve attached to the expandable ring, the prosthetic valve being adapted to replace the diseased tricuspid valve.

\* \* \* \* \*